United States Patent [19]
Rizzi et al.

[11] 3,963,699
[45] June 15, 1976

[54] SYNTHESIS OF HIGHER POLYOL FATTY ACID POLYESTERS

[75] Inventors: George Peter Rizzi; Harry Madison Taylor, both of Cincinnati, Ohio

[73] Assignee: The Procter & Gamble Company, Cincinnati, Ohio

[22] Filed: Jan. 10, 1974

[21] Appl. No.: 432,386

[52] U.S. Cl. .................... 260/234 R; 424/180; 426/611
[51] Int. Cl.² .................................... C08B 37/00
[58] Field of Search ........................ 260/234 R

[56] References Cited
UNITED STATES PATENTS

| | | | |
|---|---|---|---|
| 3,558,597 | 1/1971 | von Brachel et al. | 260/234 R |
| 3,597,417 | 8/1971 | Myhre et al. | 260/234 R |
| 3,714,144 | 1/1973 | Feuge et al. | 260/234 R |

Primary Examiner—Joseph Paul Brust
Assistant Examiner—Cary Owens
Attorney, Agent, or Firm—Jerry J. Yetter; Julius P. Filcik; Richard C. Witte

[57] ABSTRACT

A solvent-free transesterification comprising the steps of (1) heating a mixture of a polyol, a fatty acid lower alkyl ester, an alkali metal fatty acid soap, and a basic catalyst to form a homogenous melt; and (2) subsequently adding to the reaction product of step (1) excess fatty acid lower alkyl esters yields polyol fatty acid polyesters.

13 Claims, No Drawings ced to a homogenous reaction medium suitable for catalytic transesterification. One variation of this process, known as the Snell synthesis, has been employed as a means for preparing both poly- and lower esters. However, the solvents heretofore employed in such processes are difficult to separate from the final product and are characteristically toxic, therefore limiting the usefulness of such synthesis in the foods industry. Accordingly, recent efforts have been directed toward the discovery of a high yield synthesis of polyol fatty acid polyesters which does not employ toxic solvents.

SYNTHESIS OF HIGHER POLYOL FATTY ACID POLYESTERS

BACKGROUND OF THE INVENTION

This invention relates to a high yield synthesis of polyol fatty acid polyesters, sucrose polyesters in particular, via transesterification.

The food industry has recently focused attention on polyol polyesters for use as low calorie fats in food products. As a result of this attention, there is a current need for a high yield synthesis of polyol fatty acid polyesters. Historically, such syntheses have been conducted using a mutual solvent to solubilize a polyol and esters of long-chain fatty acids, thus providing a homogenous reaction medium suitable for catalytic transesterification. One variation of this process, known as the Snell synthesis, has been employed as a means for preparing both poly- and lower esters. However, the solvents heretofore employed in such processes are difficult to separate from the final product and are characteristically toxic, therefore limiting the usefulness of such synthesis in the foods industry. Accordingly, recent efforts have been directed toward the discovery of a high yield synthesis of polyol fatty acid polyesters which does not employ toxic solvents.

Other solvent-free transesterification processes are known in the art.

U.S. Pat. No. 3,521,827 discloses the preparation of sucrose polyesters by means of a solvent-free interesterification using phenyl esters. However, phenol is liberated during the reaction. Phenol is extremely toxic and caustic; contaminates the product; and is difficult to separate. Accordingly, this process does not satisfy current needs for a synthesis of polyol fatty acid polyesters for use in the foods industry.

Feuge, et al., "Preparation of Sucrose Esters by Interesterification", *Journal of the American Oil Chemical Society*, 47[s], 56–60 (1970), disclose a single stage solvent-free transesterification useful in synthesizing fatty acid esters of sucrose. However, this process is limited to the synthesis of lower esters. It has been experimentally determined that if the sucrose/methyl ester ratio of the Feuge, et al., reaction is lowered by use of excess methyl esters in an effort to synthesize polyesters, the reactants will disproportionate and pecipitate sucrose which then caramelizes to form a brittle, charred waste product. Furthermore, the Feuge, et al. article reports low yields using lower alkyl esters. The more successful Feuge, et al. synthesis uses fatty acid methyl carbitol esters as starting materials. Unfortunately, methyl carbitol is, itself, relatively toxic. Thus, the Feuge, et al. process also fails to satisfy current needs for a synthesis of polyol fatty acid polyesters useful in the foods industry.

It is therefore an object of this invention to provide a high yield synthesis of polyol fatty acid polyester.

It is a further object of this invention to provide a synthesis of polyol fatty acid polyesters which does not employ toxic solvent nor generate difficult-to-remove toxic contaminants.

It is a still further object of this invention to provide a synthesis of polyol fatty acid polyesters in which the reactants do not disproportionate thereby reducing caramelization of the polyol.

These and other objects are obtained herein as will be seen from the following disclosure.

SUMMARY OF THE INVENTION

It has now been found that high yields of polyol fatty acid polyesters can be prepared via a transesterification process which can be carried out in the absence of solvents or other contaminants. Thus, the toxicity problems of the prior art are avoided.

The synthesis disclosed herein proceeds in three stages. In the first stage, a heterogenous mixture of a polyol, fatty acid lower alkyl esters, an alkali metal fatty acid soap, and a basic catalyst is reacted to form a homogenous melt consisting of partially esterified polyol and unreacted starting materials. In the second stage, excess fatty acid lower alkyl esters are added to the melt and react with the solubilized partial esters of the polyol and the remaining unesterified polyol to form polyol fatty acid polyester. In the third stage, the polyol fatty acid polyester is separated from the reaction product. The desired polyester product is obtained in high yield. The synthesis can be conveniently carried out at relatively low temperatures and, if desired, at atmospheric pressure.

More specifically, the present invention encompasses a high yield process for synthesizing polyol fatty acid polyesters comprising the steps of:

1. heating a heterogenous mixture comprising: (i) from about 10% to about 50% by weight of a polyol; (ii) from about 40% to about 80% by weight of fatty acid lower alkyl esters; (iii) from about 1% to about 30% by weight of an alkali metal fatty acid soap; and (iv) from about 0.05% to about 5% by weight of a basic catalyst selected from the group consisting of alkali metals, alloys of two or more alkali metals, alkali metal alkoxides and alkali metal hydrides to a temperature of from about 110°C to about 180°C under a pressure of from about 0.1mm Hg to about 760mm Hg for a time sufficient to form a homogenous melt of partially esterified polyol and unreacted starting materials;
2. under the conditions of step 1, adding excess fatty acid lower alkyl esters to the reaction product of step 1 to form the polyol fatty acid polyester; and
3. separating the polyol fatty acid polyester from the reaction mixture.

DETAILED DESCRIPTION OF THE INVENTION

Objects of the present invention are achieved by providing a solvent-free process for synthesizing high yields of polyol fatty acid polyesters. The process is characterized by a unique three step reaction procedure.

Step 1

In the first step of the present process, a heterogenous mixture of (i) a polyol, (ii) fatty acid lower alkyl esters, (iii) an alkali metal fatty acid soap, and (iv) a basic catalyst is reacted to form a homogenous melt comprising partially esterified polyol and unreacted starting materials.

i. As used herein, the term "polyol" is intended to include any aliphatic or aromatic compound containing at least two free hydroxyl groups. In practicing the process disclosed herein, the selection of a suitable polyol is simply a matter of choice. For example, suitable polyols may be selected from the following classes: saturated and unsaturated straight and branched chain linear aliphatics; saturated and unsaturated cyclic aliphatics including heterocyclic aliphatics; or mononuclear and polynuclear aromatics including heterocyclic aromatics. Inasmuch as the present invention encompasses a process which does not employ toxic solvents nor generate difficult-to-remove toxic contaminants, preferred polyols are those which have utility in the foods industry. Accordingly, the carbohydrates and non-toxic glycols are preferred polyols. Carbohydrates are polyhydroxy aldehydes or polyhydroxy ketones, or substances that yield such compounds on hydrolysis. They are distributed universally in plants and animals, and make up one of the three important classes of animal foods. Carbohydrates may be subdivided into three important classes; the monosaccharides, oligosaccharides, and the polysaccharides. Monosaccharides include those carbohydrates which do not hydrolyze. Accordingly, monosaccharides suitable for use herein include, for example, glucose, mannose, galactose, arabinose, xylose, ribose, apiose, rhamnose, psicose, fructose, sorbose, tagitose, ribulose, xylulose, and erythrulose. Oligosaccharides are carbohydrates which yield only a few molecules of monosaccharides on hydrolysis. Accordingly, oligosaccharides suitable for use herein include, for example, maltose, kojibiose, nigerose, cellobiose, lactose, melibiose, gentiobiose, turanose, rutinose, trehalose, sucrose, and raffinose. Polysaccharides are those carbohydrates which yield a large number of molecules of monosaccharides on hydrolysis. Accordingly, polysaccharides suitable for use herein include, for example, amylose, glycogen, cellulose, chitin, inulin, agarose, zylans, mannan, and galactans. Another class of polyols preferred herein is the sugar alcohols. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol, and galactitol. Preferred carbohydrates and sugar alcohols suitable for use herein include, for example, xylitol, sorbitol, and sucrose.

ii. As used herein, the term "fatty acid lower alkyl esters" is intended to include the $C_1$ and $C_2$ esters of fatty acids containing about 8 or more carbon atoms, and mixtures of such esters. Suitable esters can be prepared by the reaction of diazoalkanes and fatty acids, or derived by alcoholysis from the fatty acids naturally occurring in fats and oils. If the acids are derived from fats, saturated acids predominate, but if derived from oils, unsaturated acids predominate. Accordingly, suitable fatty acid lower alkyl esters can be derived from either saturated or unsaturated fatty acids. Suitable preferred saturated fatty acids include, for example, capric lauric, palmitic, stearic, behenic, isomyristic, isomargaric, myristic, caprylic, and anteisoarachadic. Suitable preferred unsaturated fatty acids include, for example, maleic, linoleic, licanic, oleic, linolenic, and erythrogenic acids. Mixtures of fatty acids derived from soybean oil, sunflower oil, safflower oil, and corn oil are especially preferred for use herein.

Unusually high yields, i.e., greater than 90%, of polyol fatty acid polyesters have been obtained where methyl esters are used in accordance with the process herein. Accordingly, methyl esters are the preferred fatty acid lower alkyl esters.

iii. As used herein, the term "alkali metal fatty acid soap" is intended to include the alkali metal salts of saturated and unsaturated fatty acids having from about 8 to about 18 carbon atoms. Accordingly, suitable alkai metal fatty acids soaps include, for example, the lithium, sodium, potassium, rubidium, and cesium salts of fatty acids such as capric, lauric, myristic, palmitic, licanic, parinaric, and stearic acids. Mixtures of fatty acids derived from soybean oil, sunflower oil, safflower oil, and corn oil are preferred for use herein. Accordingly, preferred alkali metal fatty acid soaps include, for example, the potassium soap made from soybean oil fatty acids and the sodium soap made from sunflower oil fatty acids.

iv. The basic catalysts suitable for use herein are those selected from the group consisting of alkali metals such as sodium, lithium, and potassium; alloys of two or more alkali metals such as sodium-lithium and sodium-potassium alloys; alkali metal hydrides such as sodium, lithium and potassium hydride; and alkali metal alkoxides such as potassium t-butoxide and sodium methoxide.

In a preferred embodiment of this invention, the catalyst is dispersed in a suitable carrier so as to insure uniform distribution of the catalyst throughout the reaction mass. Suitable carriers or dispersing agents include, for example, mineral oil; hydrocarbon solvents, such as xylene; and polyol octaesters, such as sucrose octaesters. Octaesters derived from the polyol being esterified are preferred carriers since their use avoids contamination or removal problems. Preferred catalysts suitable for use herein include, for example, sodium hydride, potassium hydride, a dispersion of potassium in sucrose octaester, a dispersion of potassium in mineral oil, potassium t-butoxide, and sodium methoxide.

In carrying out step 1, the above-described reactants are combined to form a heterogenous mixture. The precise ratio of reactants can be freely selected from within the guidelines set forth hereinafter. However, routine experimentation may be necessary in order to establish the optimum concentrations for a given set of reactants. In general, the heterogenous mixture comprises from about 10% to about 50%, preferably from about 20% to about 30% by weight of a polyol; from about 40% to about 80%, preferably from about 50% to about 70% by weight of fatty acid lower alkyl esters; from about 1% to about 30%, preferably from about 5% to about 10% by weight of an alkali metal fatty acid soap; and from about 0.05% to about 5%, preferably from about 0.1% to about 0.5% by weight of a basic catalyst selected from the group consisting of alkali metals, alloys of two or more alkali metals, alkai metal alkoxides and alkali metal hydrides. The heterogenous mixture is heated to a temperature within the range of from about 110°C to about 180°C, preferably from about 130°C to about 145°C under a pressure of from about 0.1 mm Hg to about 760 mm Hg. preferably from about 0.5 mm Hg to about 25 mm Hg. Within these temperature and pressure ranges a homogenous melt of partially esterified polyol and unreacted starting materials will form in from about 1 to 4 hours.

It may be desirable to initiate the reaction by initially introducing from about 0.1% to about 1%, by weight, of catalyst and, thereafter, introducing additional catalyst as the reaction proceeds.

Step 2

In the second step of the instant process, excess fatty acid lower alkyl esters are added to the homogenous melt formed in Step 1. As used herein, the term "excess" is intended to include sufficient lower alkyl esters to raise the overall ester:polyol mole ratio above 10:1, preferably to about 16:1. Although ratios beyond 16:1 can be used, as a general rule, such ratios do not noticeably decrease reaction time or improve the yield and are therefore impractical.

It should be noted that as the transesterification proceeds, a lower alcohol is formed as a by-product. In order to promote the reaction, the alcohol by-product is preferably removed. Many removal techniques are known in the art, any one of which can be used to effectively and efficiently remove the lower alcohol. Vacuum removal both with and without an inert gas sparging has been found to promote the reaction. However, for practical purposes, simple distillation under atmospheric pressure has been found to be sufficient. In any event, the formation of a lower alcohol presents no significant obstacle to the use of the instant process by the foods industry.

Step 3

In the third step of the process, the polyol fatty acid polyesters formed in step 2 are separated from the reaction product containing polyesters, alcohol, and unreacted starting materials. Separation can be accomplished by any of the routinely used separation procedures. Distillation or solvent extraction are preferred due to their simplicity and economy.

The following examples are intended to further clarify the invention and should not be construed as limitations.

EXAMPLE I

Preparation of Sucrose Polyester from Sucrose and Methyl Esters

A 1,000 milliliter resin kettle equipped with a mechanical stirrer, thermometer, dropping funnel, and a distillation head arranged for vacuum take off was charged with finely powdered sucrose (25.5 gram, 0.0745 moles), soy methyl esters (73.5 milliliters, 0.224 moles) and anhydrous potassium-soap made from soy methyl esters (10.0 grams). Heat was supplied via a large magnetically stirred oil bath arranged below the kettle and the mixture was deoxygenated under 15 millimeters vacuum for 1.25 hours at 95°C. On cooling to 55°C sodium hydride, 0.1% (0.178 grams of 56% dispersion in mineral oil) was added and the mixture was reacted at 145°-148°C/15 millimeters for 2 hours during which time the mix changed from a white slurry to a light brown translucent liquid. The mix was cooled to approximately 90°C treated with a second 0.178 gram potion of sodium hydride dispersion and reacted 1.5 hours at 150°C/10 millimeters. The mixture was cooled somewhat, diluted with 297.0 milliliters of methyl esters from soybean oil, reheated to 150°C/10 millimeters for one hour, cooled, treated with a third portion of sodium hydride (0.178 grams), reheated to 150°C/10 millimeters for three hours and finally cooled to room temperature. During 7.5 hours about 25–30 milliliters of liquid distillate collected in vacuum traps at dry ice:isopropanol temperature. The crude reaction product was treated with 1 milliliter of acetic acid and washed by stirring and decantation with 5400 milliliters of methanol (9 × 600 milliliters). Ice cooling prior to decantation greatly facilitated the separation of the lower, sucrose polyester phase. The clear brown sucrose polyester phase was freed of last traces of methanol by gentle heat under vacuum prior to bleaching with 10 grams of Filtrol clay at 100°C/2.5 hours/1 atmosphere. The neat mixture of sucrose polyester and clay was cooled, dissolved in hexane and the resulting slurry was vacuum filtered. Evaporation of hexane under vacuum gave 143.2 grams of light yellow oil; having a hydroxyl value of 18.7. The yield based on sugar was 86% sucrose polyesters.

In the above procedure, the sucrose is replaced by an equivalent amount of propylene glycol, glycerol, pentaerythritol, glucose, xylitol and sorbitol, respectively, and the corresponding polyol fatty acid polyesters are obtained.

In the above procedure, the sodium hydride is replaced by an equivalent amount of potassium metal, lithium metal, sodium-potassium alloy, potassium hydride, and lithium hydride, potassium methoxide, and potassium t-butoxide, respectively, and equivalent results are secured.

EXAMPLE II

Preparation of Sucrose Polyester From Sucrose and Soybean Methyl Esters Under Atmospheric Pressure A mixture containing powdered sucrose (2.52 grams), partially hardened (I.V. 57) soybean methyl esters (6.48 grams) and anhydrous potassium soap made from the same methyl esters (1.0 grams) was homogenized for 10 minutes in a high shear Omnimixer. The slurry was treated with 0.2% by weight of sodium hydride (56% dispersion mineral oil) and reacted 2 hours at 147°C under nitrogen (provision was made for distillation of methanol evolved in the reaction). The one-phase mixture containing lower esters was treated with a second 0.2% of sodium hydride and 31.8 milliliters of additional methyl esters. After reacting another 6 hours at 147°C, the final product was cooled and washed 5 times with 100 milliliters of hot ethanol to remove soap and excess methyl esters. Final removal of ethanol under vacuum gave 15.7 grams of an off-white solid; yield based on sucrose was 90%. Quantitative NMR analysis indicated that the product contained less than 6% methyl ester and TLC showed no free fatty acids present.

As a preferred embodiment of this invention, it has been found that the alkali metal fatty acid soap used herein can be formed in situ by saponifying an alkali metal hydroxide using the fatty acid lower alkyl ester reactant. Accordingly, a preferred embodiment of the process disclosed herein comprises the steps of:

1. Heating a mixture of a fatty acid lower alkyl ester and an alkali metal hydroxide to a temperature of from about 100°C to about 140°C, preferably about 120°C under atmospheric pressure to form an emulsion comprising from about 5% to about 30%, preferably from about 7% to about 15% by weight of the corresponding alkali metal fatty acid soap and lower alkyl ester;

2. Adding to the reaction product of Step (1) from about 10% to about 50%, preferably from about 20% to about 30% by weight of a polyol and from about 0.05% to about 5%, preferably from about 0.1% to about 0.5% by weight of a basic catalyst selected from the group consisting of alkali metals, alloys of two or more alkali metals, alkali metal alkoxides, and alkali metal hydrides to form a heterogenous mixture;

3. Heating the heterogenous mixture formed in Step (2) to a temperature of from about 110°C to about 180°C, preferably from about 130°C to about 145°C under a pressure of from about 0.1 mm Hg to about 760 mm Hg, preferably from about 0.5 mm Hg to about 25 mm Hg to form a homogenous melt of partially esterified polyol and unreacted starting materials;

4. Under the conditions of Step (3), adding excess fatty acid lower alkyl esters to the reaction product of Step (3) to form the polyol fatty acid polyester; and 5. Separating the polyol fatty acid polyester from the reaction mixture.

The weight percentages of reactants used to form the fatty acid soap emulsion in Step (1) obviously depend upon the molecular weight of the particular alkali metal hydroxide employed. Inasmuch as the alkali metals vary in molecular weight between about 7 (lithium) and about 133 (cesium), the reactant weight prcentages vary appreciably. Notwithstanding this variability, calculation of the useful ranges of reactant weight percentages can be determined by routine methods. By way of example, it has been determined that when using potassium hydroxide (molecular weight of about 39), the mixture of Step (1) comprises from about 94% to about 99% by weight fatty acid lower alkyl esters and from about 1% to about 6% by weight potassium hydroxide.

The following example is intended to further clarify the preferred embodiments and should not be construed as a limitation.

EXAMPLE III

Preparation of Sucrose Polyester from Sucrose and Soybean Methyl Esters Using Potassium Dispersion Soybean methyl esters (2.86 kilograms, I.V. = 132–135) were mixed with potassium hydroxide (63 grams of 85% KOH dissolved in 300 milliliters methanol) at atmospheric pessure and heated to 120°C with agitation. After 2 hours a smooth textured emulsion was formed and powdered sucrose (1.04 kilograms) was added to the mixture. The pressure was reduced to 5 millimeters Hg to remove any moisture and methanol and 30 grams of a potassium dispersion (30% potassium, 70% light mineral oil) was added. This mixture was reacted for 2 hours at 145°C to form a one-phase mixture. Excess soybean methyl esters (12.17 kilograms) were then added and the reaction continued for 4 hours under the above conditions. The system was then allowed to cool overnight and started up the following day by adding more potassium dispersion (30 grams of 30/70 dispersion) and returning to 145°C and 5 millimeters Hg for 4 hours. The reaction mixture was then acidified with glacial acetic acid (250 milliliters). NMR analysis showed the final mixture to contain 49.8% methyl esters. Allowing for the soap formed during the first portion of the reaction and by reaction of the catalyst, this indicates a sucrose polyester yield of 97 to 98% based on sucrose.

In the above procedure, sucrose polyester was prepared without significant caramelization of the sucrose reactant.

In the above procedure, the soybean methyl esters are replaced by an equivalent amount of sunflower oil methyl esters, safflower oil methyl esters, and corn oil methyl esters and the corresponding sucrose fatty acid polyesters are obtained.

Polyol fatty acid polyesters prepared in accordance with the above disclosure are suitable for use as low calorie fats in various food products. For example, U.S. Pat. No. 3,600,186, granted August 17, 1971, teaches the use of polyol fatty acid polyesters as low calorie fats in cooking and salad oils. The following example illustrates low calorie fat-containing food compositions wherein the fat comprises a polyol fatty acid polyester prepared according to the process of the present invention.

EXAMPLE IV

Food Compositions Containing Polyol Fatty Acid Polyesters Salad oils are prepared as follows:

| Ingredients | Percent by Weight |
|---|---|
| (A) | |
| Refined, bleached and lightly hydrogenated soybean oil | 50 |
| Sucrose octaester of soybean oil fatty acid | 50 |
| (B) | |
| Refined cottonseed oil | 90 |
| Sorbitol pentaoleate | 10 |
| (C) | |
| Sucrose octaoleate, 100 | |
| (D) | |
| Erythritol polyester of olive oil fatty acid | 100 |
| (E) | |
| 50/50 Blend of cottonseed oil and soybean oil | 50 |
| Olive oil | 25 |
| Erythritol polyester of sunflower oil | 25 |

What is claimed is:

1. A solvent-free, low temperature process for synthesizing polyol fatty acid polyesters consisting essentially of:
   1. Heating a mixture of a polyol selected from the group consisting of monosaccharides, disaccharides and sugar alcohols, a fatty acid $C_{1-2}$ alkyl ester, an alkali metal fatty acid soap, and a basic catalyst selected from the group consisting of alkali metal, alloys of alkali metals, alkali metal hydrides and alkali metal alkoxides to a temperature of from about 110°C to about 180°C at a pressure of from about 0.1 mm of Hg to about 760 mm of Hg to form a homogenous melt of partially esterified polyol and unreacted starting materials;
   2. Under the conditions of Step (1) adding excess fatty acid lower alkyl esters to the reaction product of Step (1) to form the polyol fatty acid polyester; and
   3. Separating the polyol fatty acid polyester from the reaction product of Step (2).

2. A process according to claim 1 wherein the polyol is a disaccharide.

3. A process according to claim 1 wherein the polyol is selected from the group consisting of sucrose, xylitol, and sorbitol.

4. A process according to claim 1 wherein the temperature is from about 135°C to about 145°C.

5. A process according to claim 1 wherein the fatty acid $C_{1-2}$ alkyl esters are fatty acid methyl esters.

6. A process according to claim 5 wherein the methyl esters are derived from natural oils selected from the group consisting of soybean oil, sunflower oil, safflower oil and corn oil.

7. A process according to claim 1 wherein the catalyst is selected from the group consisting of potassium hydride, sodium hydride, a dispersion of potassium in sucrose octaester, a dispersion of potassium in mineral oil, potassium t-butoxide and sodium methoxide.

8. A solvent-free, low temperature process for synthesizing polyol fatty acid polyesters consisting essentially of:

1. Heating a mixture comprising (i) from about 10% to about 50% by weight of a polyol selected from the group consisting of monosaccharides, disaccharides and sugar alcohols, (ii) from about 40% to about 80% by weight of fatty acid $C_{1-2}$ alkyl esters, (iii) from about 1% to about 30% by weight of an alkali metal fatty acid soap, and (iv) from about 0.05% to about 5% by weight of a basic catalyst selected from the group consisting of alkali metals, alloy of two or more alkali metals, alkali metal alkoxides, and alkali metal hydrides to a temperature from about 110°C to about 180°C at a pressure of from about 0.1 mm of Hg to about 760 mm of Hg to form a homogenous melt of partially esterified polyol and unreacted starting materials;
2. Under the conditions of Step (1) adding excess fatty acid $C_{1-2}$ alkyl esters to the reaction product of Step (1) to form the polyol fatty acid polyester; and
3. Separating the polyol fatty acid polyester from the reaction product of Step (2.).

9. A process according to claim 8 wherein the polyol is sucrose.

10. A solvent-free, low temperature process for synthesizing poly fatty polyesters consisting essentially of:
   1. Heating a mixture of a fatty acid $C_{1-2}$ alkyl ester and an alkali metal hydroxide to a temperature of from about 100°C to about 140°C under atmospheric pressure to form an emulsion comprising from about 5% to about 30%, by weight, of the corresponding alkali metal fatty acid soap and $C_{1-2}$ alkyl ester;
   2. Adding to the reaction product of Step (1) from about 10% to about 50% by weight of a polyol and from about 0.05% to about 5% by weight of a basic catalyst selected from the group consisting of alkali metals, alloys of two or more alkali metals, alkali metal alkoxides, and alkali metal hydrides to form a heterogenous mixture;
   3. Heating the heterogenous mixture formed in Step (2) to a temperature of from about 110°C to about 180°C under a pressure of from about 0.1 mm Hg to about 760 mm Hg to form a homogeneous melt of partially esterified polyol and unreacted starting materials;
   4. Under the conditions of Step (3), adding excess fatty acid $C_{1-2}$ alkyl esters to the reaction product of step (3) to form the polyol fatty acid polyester; and
   5. Separating the polyol fatty acid polyester from the reaction mixture.

11. A process according to claim 10 wherein the alkali metal hydroxide is potassium hydroxide.

12. A process according to claim 10 wherein the polyol is sucrose.

13. A process according to claim 10 wherein the fatty acid $C_{1-2}$ alkyl esters are fatty acid methyl esters derived from natural oils selected from the group consisting of soybean oil, sunflower oil, safflower oil, and corn oil.

* * * * *